United States Patent [19]

Abrahamsson et al.

[11] Patent Number: 4,781,297

[45] Date of Patent: Nov. 1, 1988

[54] READILY TEARABLE PACKAGE FOR STERILE ARTICLES

[75] Inventors: Rolf Abrahamsson, Mölndal; Mats Berencreutz, Mölnlycke, both of Sweden

[73] Assignee: Molnlycke AB, Gothenburg, Sweden

[21] Appl. No.: 26,366

[22] PCT Filed: Jun. 10, 1986

[86] PCT No.: PCT/SE86/00277

§ 371 Date: Jan. 15, 1987

§ 102(e) Date: Jan. 15, 1987

[87] PCT Pub. No.: WO86/07334

PCT Pub. Date: Dec. 18, 1986

[30] Foreign Application Priority Data

Jun. 11, 1985 [SE] Sweden .............................. 8502888

[51] Int. Cl.⁴ .......................................... B65D 75/58
[52] U.S. Cl. .................................. 206/610; 206/439; 206/461; 206/484.1; 206/634; 383/120
[58] Field of Search ............... 206/438, 439, 605, 607, 206/610, 45.33, 634, 632, 484, 461, 466, 484.1; 383/120

[56] References Cited

U.S. PATENT DOCUMENTS

| | | |
|---|---|---|
| 1,907,675 | 5/1933 | Rosen ............................ 206/45.33 |
| 3,036,700 | 5/1962 | Krug . |
| 3,143,276 | 8/1964 | Nichols ........................... 383/120 X |
| 3,186,628 | 6/1965 | Rolide ............................ 206/484 X |
| 3,235,168 | 2/1966 | Nichols ........................... 383/120 X |
| 3,357,549 | 12/1967 | Staiti . |
| 3,396,900 | 8/1968 | Lucas . |
| 3,478,868 | 11/1969 | Nerenberg et al. ............... 206/439 |
| 3,642,126 | 2/1972 | Kurtz et al. . |
| 4,098,406 | 7/1978 | Otten et al. . |
| 4,176,746 | 12/1979 | Kooi . |
| 4,367,816 | 1/1983 | Wilkes . |

FOREIGN PATENT DOCUMENTS

| | | |
|---|---|---|
| 0060411 | 9/1982 | European Pat. Off. . |
| 0081791 | 6/1983 | European Pat. Off. . |
| 2462351 | 3/1981 | France ............................. 206/438 |
| 0346968 | 7/1972 | Sweden . |
| 0385683 | 7/1976 | Sweden . |
| 0388179 | 9/1976 | Sweden . |

*Primary Examiner*—Stephen Marcus
*Assistant Examiner*—Bryon Gehman
*Attorney, Agent, or Firm*—Young & Thompson

[57] ABSTRACT

A package for sterile articles, comprising a paper part and a plastic part connected to the paper part along longitudinal and transverse lines. The plastic part comprises a linearly oriented plastic film material which can be torn in its direction of orientation. This direction of orientation is parallel to those longitudinal lines, and tear indications on the plastic part at one end of the package are parallel to and disposed between but closely adjacent those longitudinal lines. The paper part has edge portions that are folded over toward each other. The longitudinal lines secure the plastic part to the outer sides of those folded-over portions, said folded-over portions having free edges that are between and spaced a substantially distance from the tear indications. There is a sterile article in the package, those edge portions being folded over the edges of the sterile article.

2 Claims, 2 Drawing Sheets

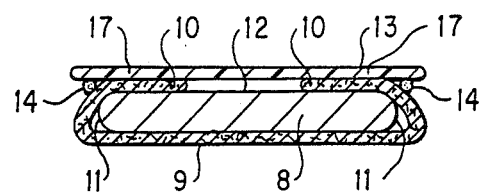
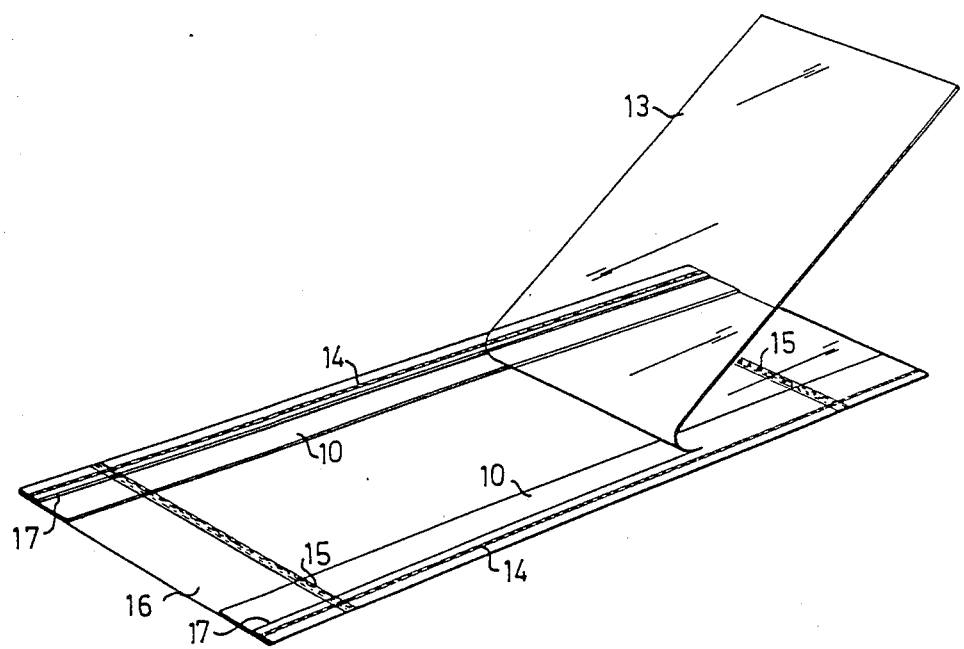

READILY TEARABLE PACKAGE FOR STERILE ARTICLES

The present invention relates to a package intended for sterile articles. A most essential feature in packages of this type is that total sterility for the enclosed article is secured during handling.

If gas or steam is chosen as a sterilization medium, the package must of course be gas and vapor permeable. To this end, such packages for sterile articles should not be made of plastic alone, or paper coated with plastic all over its surface, because the packages would then burst during the gas sterilization process.

Opening of a sterile package often takes place in a sterile environment such as an operating room. It is fundamental to make sure that the opening procedure does not give rise to contamination of the surroundings, for example by release of fiber or dust particles. Although sterile, such particles could easily cause inflammatory reactions when coming into contact with body tissues in an operation wound.

Another essential demand is to allow for the sterilized article to be packed in such a manner that its sterility is preserved when taken out of the package.

The packages used today for small or thin articles normally consist of two sheets of paper sealed together along their edge margins, whereas thick or bulky articles are packed in plastic trays heat-sealed to a paper lid. These two types of package are opened by tearing off the seals. Since sealing is usually performed by melting together a sheet of paper coated with a lacquer and a sheet of paper without coating, opening of a conventionally produced package will result in a certain amount of paper being ripped off when breaking the seal open and, as an inevitable consequence, the appearance of loose fiber particles.

A further significant factor associated with such packages is the problem of attaining seams which are tight and strong enough to provide sterility for their contents, but still easily pulled apart without splitting the paper when opening the package.

If the package is ripped as a result of too strong heat seal welds, the contents will most probably be contaminated by the rugged tear edges, and the article which is no longer sterile has to be discarded. With the present invention there is obtained a package intended for sterile articles which, when opened, does not give off fiber particles and which eliminates the problem of adjusting the seals or bonds to the desired strength.

A package for sterile articles made according to the invention is primarily distinguished in that it includes a paper web part (1) to which is joined a plastic web part (2), said web parts together serving to accommodate at least one article (8), whereby the plastic web part is formed of a film made of a linearly oriented plastic material, is tearable in the direction of orientation of the plastic material, and preferably has one or more tear indications (5) for opening the package.

In order to break open a conventional package, the interconnected package-forming webs must be pulled apart, as previously mentioned. Such tearing will require the use of both hands, which after having been in touch with the non-sterile outer surfaces of the package are no longer sterile. Emptying the package by turning it upside down and letting the contents fall out and down onto a sterile surface would involve a considerable risk of contamination, since the article could then easily come into contact with the ripped non-sterile sealing surfaces of the package. To enable removal of the sterile article from the package with its sterility intact, there is thus needed the assistance of a second person.

A further disadvantage in conjunction with the opening of conventional packages is that their contents tend to slip aside thereby easily getting in touch with the non-sterile, ripped surfaces, or they will just fall right out of the package and down onto a non-sterile surface.

With a suitable embodiment of a package according to the invention, the aforesaid drawbacks are overcome by at least one portion of the paper web part being folded in over the contents of the package; by the plastic web part at least partially overlapping the inwardly folded portion of the paper web part which is then at least partially covered by the plastic web part; by the plastic web part being both transversely and longitudinally connected to the paper web part; and by the plastic web part being provided with tear indications located beyond the connecting lines with imaginary tear lines made inwardly of and immediately adjacent two parallel connecting lines, the orientation of the linear plastic material being such that the plastic web part can be torn along said connecting lines so that the sterilized contents of the package is retained between the folded-over paper portion and the remaining paper web part after the package has been opened and the plastic web part torn off.

The invention will be described in more detail below with reference to two exemplary embodiments shown in the accompanying drawings, of which FIG. 1a is a plan view of a first embodiment of a package according to the invention as seen from above;

FIG. 1b is a cross section along the line A—A in FIG. 1a;

FIG. 2b is a cross section along the line B—B in FIG. 2a, and

Figure 2A:
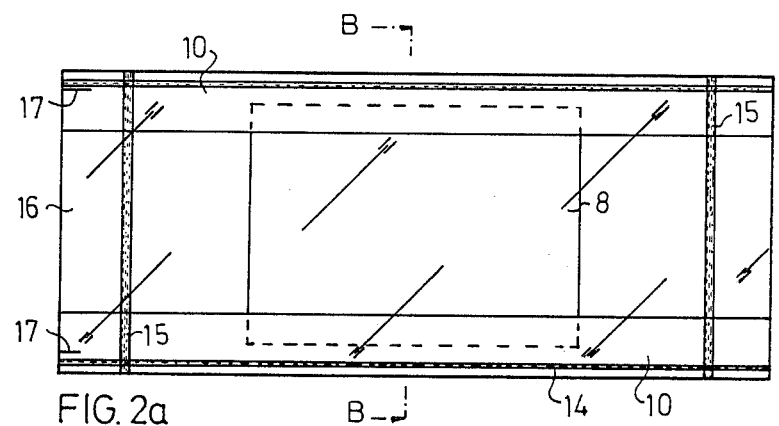
FIG. 2a is a plan view, also seen from above, of a second embodiment of the inventive package.

FIG. 3 finally is a perspective view of the embodiment as seen in FIGS. 2a and 2b showing the package partially torn apart.

Figure 1A:
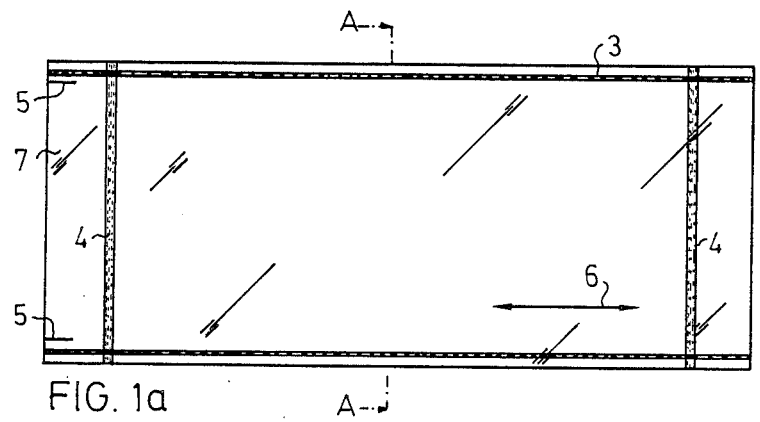
Figure 1B:
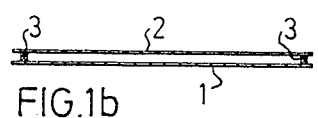

According to the embodiment of the inventive package as shown in FIGS. 1a and 1b, a sheet of paper 1 and a plastic film 2 are interconnected along two parallel side edges. The plastic material used is a linearly oriented polyethylene film which is tearable along its direction of orientation without the need of mechanically applied tear lines in the plastic material. An example of such a plastic film is Favorite CPL 5500, made by Favorite Plastic Corporation.

As binder 3 can be used a glue, preferably hot melt. The sheet of paper is coated with a lacquer, which enables the application of heat cross seals 4 on the package. Other types of cross seal are also conceivable such as cold seals, for example.

Two tear indications 5, disposed near the glue lines 3 in the area of the plastic web lying beyond the cross seal at one end portion of the package, are so arranged in relation to the plastic web that their lines of elongation coincide with the linear direction of orientation thereof.

In order to open the package, a flap 7 formed between the tear indications 5 is lifted, whereafter the plastic web can be torn open due to its linearity along the extension of the tear indications parallel with the glue lines.

The method outlined above involves the advantages that no spread of loose fiber particles from the package will occur since opening takes place by tearing the plastic material, and that the bonds on the package can be made without considering any demands on tearability, obviating simultaneously the problems associated with too weak bonds. Also, optimal security is attained with regard to maintaining sterility of the enclosed article.

According to the second embodiment shown in FIGS. 2a and 2b, a sterilized article 8 is applied with one of its side surfaces abutting against the paper web part 9, which is rectangular in shape and has two opposing edge portions 10 bent in over two edges 11 of the article and partially in over the opposite side surface 12 thereof. The plastic web part 13 overlaps the inwardly bent edge portions 10 of the paper web part and is sealed thereto, preferably by hot melt 14, parallel with and close to the fold lines of the edge portions 10. At its ends, the package further has cross seals 15, the portion of the plastic web part located beyond the cross seal at one end 16 of the package being provided with tear indications 17 made in the linear direction of orientation of the plastic material and aligned with the bonds 14 connecting the plastic web part to the inwardly bent edge portions of the paper web part. The tear indications are disposed close to the edge bonds and with their lines of elongation extending lengthwise of the bent-over edge portions 10 of the paper web part. The package is opened by tearing off the plastic web part along the elongation of the tear indications, as shown in FIG. 3.

By means of the portions 10 of the paper web part being bent in over the edges of the contents in the package, the article in the package when opened is prevented from coming into contact with the ripped, non-sterile surfaces of the plastic material. The edge flaps further serve to minimze the risk of the contents sliding out when opening the package, said flaps also enabling one person along to empty the package by grasping the article between the main portion of the paper web part and one inwardly bent portion with one hand, the other hand then being free to fold off the opposite, inwardly bent portion from the article. In doing so, the article is allowed to fall out of the package and down onto a sterile surface without the risk of touching any non-sterile surfaces on the package such as the ripped edges of the plastic web part.

A further advantage is gained in that the foldings and the plastic together render the package more flexible, thus enabling it to be utilized also for bulky and thick articles, as well as the resulting profits with regard to freedom of loose fibers and increased bond strength.

The invention is not limited to the embodiments described above but also encompasses any modification falling within the scope of the appended claims.

We claim:

1. A package for a sterile article, comprising a paper part and a plastic part secured to said paper part along opposing longitudinal and opposing transverse lines in intersecting sealing relationship to define a package cavity adapted to accommodate said sterile article, said package having at least one end portion including a portion of said plastic part extending outwardly from one said transverse line, said plastic part comprising a linearly oriented plastic film material which can be torn in its direction of orientation, said direction of orientation being parallel to said longitudinal lines, said paper part having opposing free edge portions parallel to said longitudinal lines that are folded over toward each other and terminating within said package cavity, said longitudinal lines being disposed on said folded over free edge portions of said paper part, and tear indications on the portion of the plastic part in said outwardly extending end portion of the package parallel to and between but closely adjacent said longitudinal lines, said opposing free edge portions terminating between and spaced a substantial distance from said tear indications and said longitudinal lines.

2. The package of claim 1 wherein said tear indications are positioned closer to said longitudinal lines than to said opposing free edge portions.

* * * * *